(12) United States Patent
Rini et al.

(10) Patent No.: US 8,104,533 B2
(45) Date of Patent: Jan. 31, 2012

(54) SPRAY NOZZLE APPARATUS AND METHOD OF USE

(75) Inventors: Daniel P. Rini, Orlando, FL (US); H. Randolph Anderson, Clermont, FL (US); Guochang Zhao, Orlando, FL (US)

(73) Assignee: Rini Technologies, Inc., Oveido, FL (US)

( * ) Notice: Subject to any disclaimer, the term of this patent is extended or adjusted under 35 U.S.C. 154(b) by 564 days.

(21) Appl. No.: 12/237,003

(22) Filed: Sep. 24, 2008

(65) Prior Publication Data

US 2009/0014562 A1 Jan. 15, 2009

Related U.S. Application Data

(60) Division of application No. 11/929,578, filed on Oct. 30, 2007, which is a continuation of application No. 10/342,669, filed on Jan. 14, 2003, now abandoned.

(60) Provisional application No. 60/398,244, filed on Jul. 24, 2002, provisional application No. 60/353,291, filed on Feb. 1, 2002.

(51) Int. Cl.
*F28F 7/02* (2006.01)
(52) U.S. Cl. .................. 165/80.4; 165/104.19
(58) Field of Classification Search .............. 165/80.4, 165/80.5, 104.19, 104.33
See application file for complete search history.

(56) References Cited

U.S. PATENT DOCUMENTS

| 5,220,804 A * | 6/1993 | Tilton et al. ............... 62/64 |
| 5,353,865 A | 10/1994 | Adiutori et al. |
| 5,606,201 A | 2/1997 | Lutz |
| 5,718,117 A | 2/1998 | McDunn et al. |
| 5,854,092 A | 12/1998 | Root et al. |
| 5,934,555 A * | 8/1999 | Dobbeling et al. ............ 239/11 |
| 2003/0155434 A1 | 8/2003 | Rini et al. |

FOREIGN PATENT DOCUMENTS

| GB | 1 356 114 | 6/1974 |
| JP | 62 119947 | 6/1987 |

* cited by examiner

*Primary Examiner* — Teresa Walberg
(74) *Attorney, Agent, or Firm* — Saliwanchik, Lloyd & Eisenschenk

(57) ABSTRACT

The subject invention pertains to a spray nozzle apparatus and method of use. The subject spray nozzle can be used to spray atomized fluid. The atomized fluid can then be incident on a heated surface such that heat is transferred from the heated surface to the atomized fluid. The subject invention also relates to a spray-cooling system and method of use. The subject spray-cooling system can incorporate a spray nozzle and a heat transfer plate. A device to be cooled, such as a laser diode, microwave amplifier, or other high power electrical device, can be placed in direct thermal contact with the heat transfer plate. The spray from the spray nozzle can then be sprayed onto the heat transfer plate. In a specific embodiment, a cellular transfer plate can be used and the spray from the spray nozzle can be sprayed into a cellular cavity or compartment, within the heat transfer plate. Heat is transferred from the heat source to the sprayed liquid via the wall of the heat transfer plate. The heat transfer plate can be attached to the spray nozzle housing, such that as the sprayed liquid exits the spray nozzle housing, the sprayed liquid enters a cellular cavity of the cellular heat transfer plate. Removing the cellular heat transfer plate from the spray-cooling assembly can allow the apparatus to be used as a conventional spray nozzle.

67 Claims, 10 Drawing Sheets

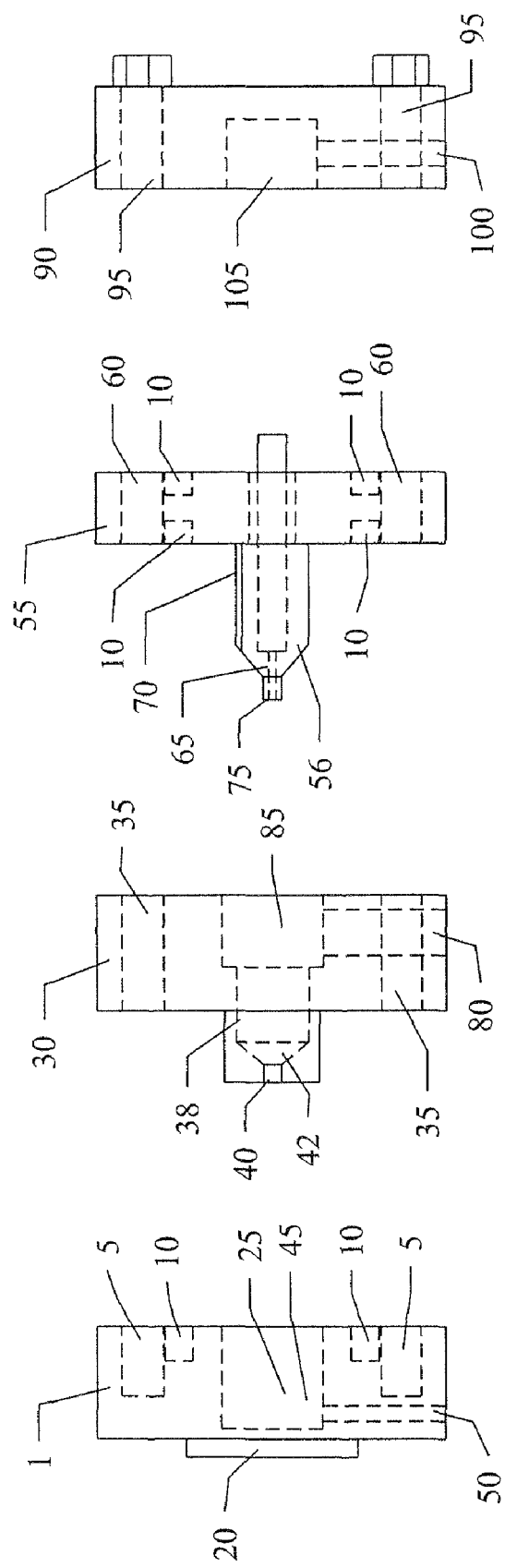

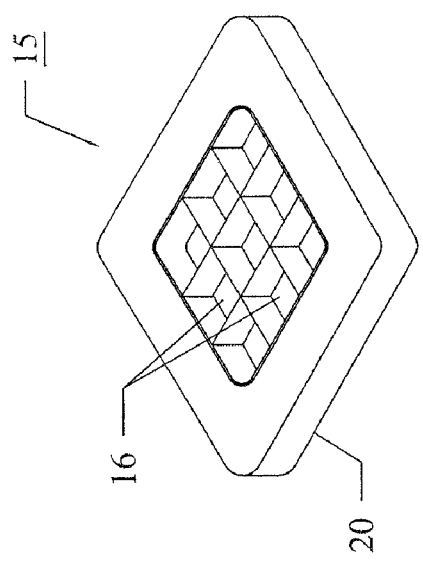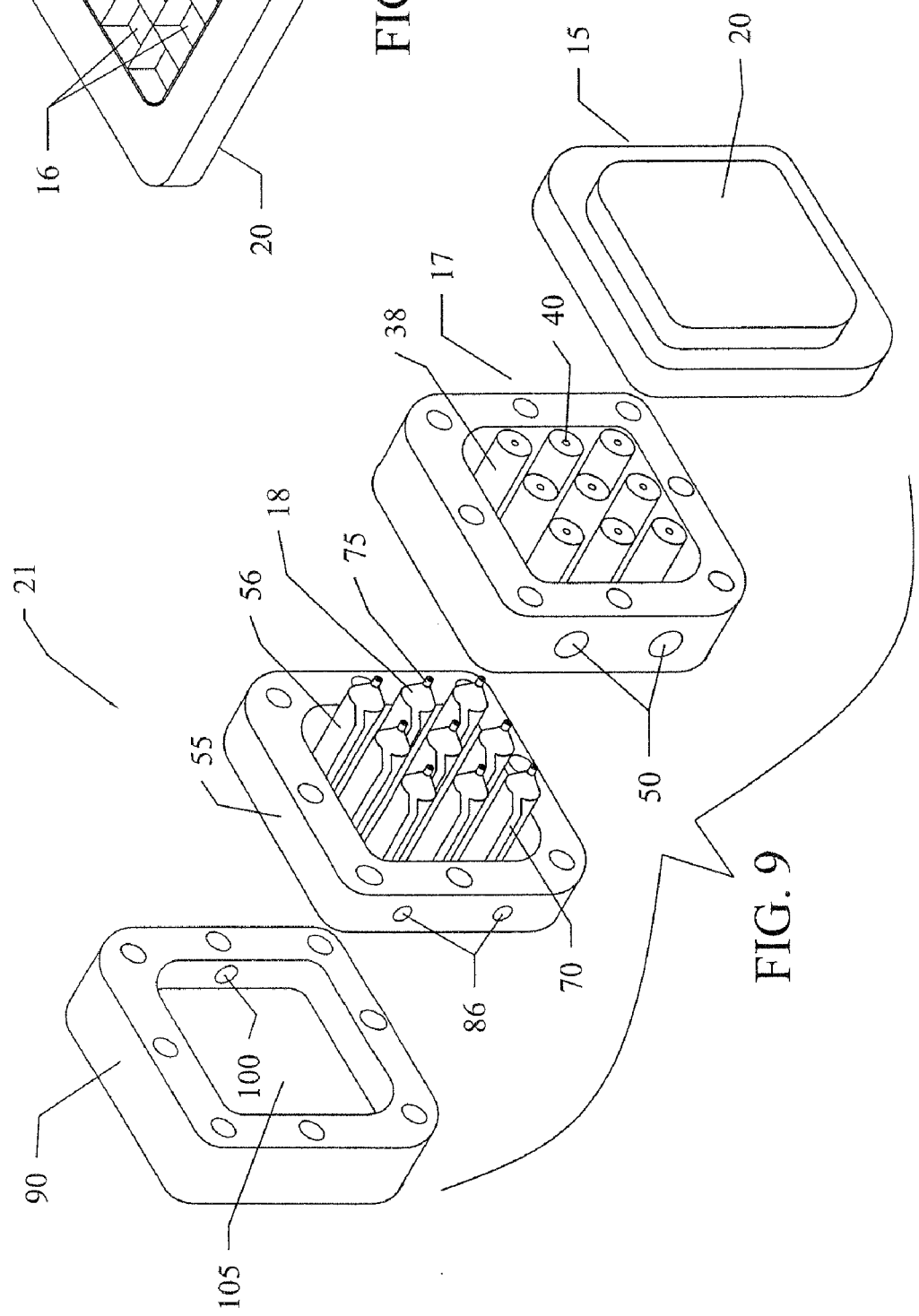

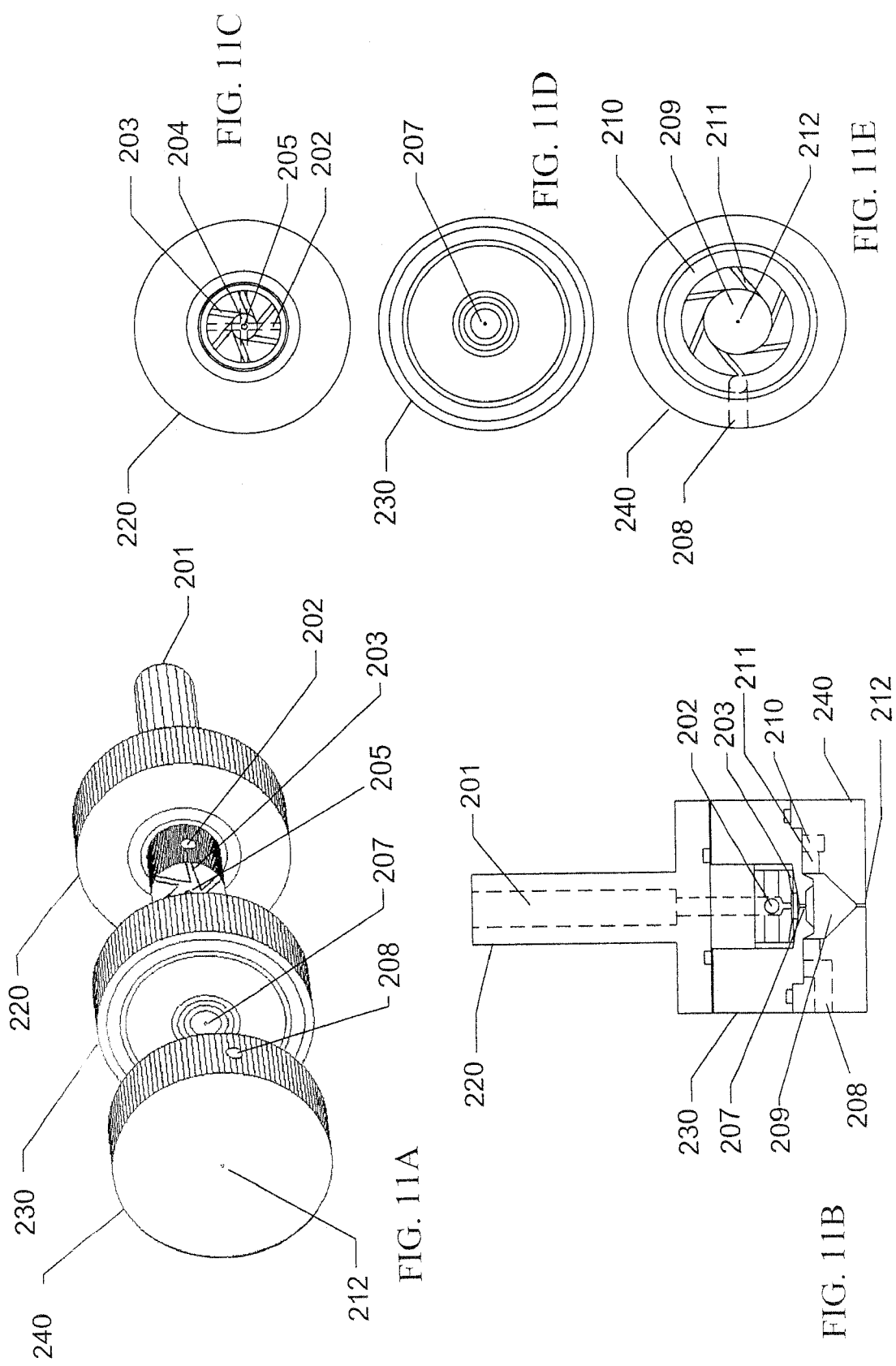

SPRAY NOZZLE APPARATUS AND METHOD OF USE

CROSS-REFERENCE TO RELATED APPLICATIONS

The present application is a divisional of U.S. patent application Ser. No. 11/929,587, filed on Oct. 30, 2007, which is a continuation of U.S. patent application Ser. No. 10/342,669, filed on Jan. 14, 2003, which claims the benefit of U.S. Provisional Patent Application Ser. No. 60/398,244, filed Jul. 24, 2002 and U.S. Provisional Patent Application Ser. No. 60/353,291, filed Feb. 1, 2002, all of which are hereby incorporated by reference in their entirety.

BACKGROUND OF THE INVENTION

In recent years, attention has been focused on methods of high heat flux removal at low surface temperatures. This is due to the advancing requirements of the electronics industry that prevent high temperature heat transfer due to the operating conditions of electronics. Though the heat transfer process is very complex and still not completely understood, many evaporative spray cooling experiments have been performed which indicated the high heat removal capability of this cooling technique. The spray technique generally works in the following way; a spray nozzle is use to atomize a pressurized liquid, and the resulting droplets are impinged onto the heated surface. A thin film of liquid is formed on the heat transfer surface in which nucleate boiling takes place. The droplet impingement simultaneously causes intense convection and free surface evaporation. When a liquid with high latent heat of vaporization (such as water) is used, over 1 kW/cm$^2$ of heat removal capability has been demonstrated.

The temperature of the cooled surface is determined by the boiling point of the liquid. Since the resulting heat transfer coefficient is very large (50,000 to 500,000 W/m$^2$ C) the surface temperature will be only a few ° C. above the boiling point of the liquid.

This type of cooling technique is most appropriately implemented when used to cool high heat flux devices such as power electronics, microwave and radio frequency generators, and diode laser arrays.

As stated above, diode laser arrays and microwave generators are devices that can be cooled with this type of impinging spray technology. Current market forces are driving these devices to increased power and size requirements. As a result, high heat flux devices are now being designed with surface areas much larger than 2 cm$^2$. New high heat flux devices may be 10 cm$^2$ to 1000 cm$^2$, or larger. Spray cooling techniques offer the ability to provide superior cooling if atomizer nozzle and nozzle arrays can be developed that provide optimal cooling characteristics. Typical atomizer nozzles for painting, fuel atomization, and humidification do not meet the cooling need of these next generation high power electronic devices.

BRIEF SUMMARY OF THE INVENTION

The subject invention pertains to a spray nozzle apparatus and method of use. The subject spray nozzle can be used to spray atomized fluid. The atomized fluid can then be incident on a heated surface such that heat is transferred from the heated surface to the atomized fluid. The subject spray nozzle can incorporate a means to initially destabilize a primary fluid inputted into the spray nozzle. A secondary fluid can then interact with the initial destabilized primary fluid so as to further destabilize the primary fluid such a combined flow of the primary fluid and the secondary fluid exits the spray nozzle and is atomized upon exiting the spray nozzle.

The subject invention also relates to a spray-cooling system and method of use. The subject spray-cooling system can incorporate a spray nozzle and a heat transfer plate. A device to be cooled, such as a laser diode, microwave amplifier, or other high power electrical device, can be placed in direct thermal contact with the heat transfer plate. The spray from the spray nozzle can then be sprayed onto the heat transfer plate. In a specific embodiment, a cellular transfer plate can be used and the spray from the spray nozzle can be sprayed into a cellular cavity or compartment, within the heat transfer plate. Heat is transferred from the heat source to the sprayed liquid via the wall of the heat transfer plate. The heat transfer plate can be attached to the spray nozzle housing, such that as the sprayed liquid exits the spray nozzle housing, the sprayed liquid enters a cellular cavity of the cellular heat transfer plate. Removing the cellular heat transfer plate from the spray-cooling assembly can allow the apparatus to be used as a conventional spray nozzle.

In a specific embodiment, the subject spray nozzle housing can house an inner nozzle portion and an outer nozzle portion. In a specific embodiment, the inner nozzle portion can incorporate swirl-developing channels. The inner spray nozzle can be placed within the outer nozzle portion. In a specific embodiment, the outer nozzle portion can be integral with the nozzle housing. A primary fluid can enter the inner nozzle via a connection to a primary fluid manifold or other fluid delivery means, flow through the inner nozzle, and exit the inner nozzle via, for example, one or more openings at, or near, the tip of the inner nozzle. In a specific embodiment, the primary fluid can flow through the inner nozzle portion via one or more fluid channels, such as holes drilled through the inner nozzle portion. The primary fluid exiting the inner nozzle portion can be initial destabilized as the primary fluid is inputted to a mixing chamber.

A secondary fluid can interact with the primary fluid as the primary fluid exits the tip, or near the tip, of the inner nozzle and enters the mixing chamber such that the primary fluid is further destabilized by the interaction with the secondary fluid. In a specific embodiment, secondary fluid can enter an outer cavity, or mixing chamber, surrounding the outside of the inner nozzle via a secondary fluid inlet port. The secondary fluid can flow from the outer cavity in channels cut on the outside of the inner nozzle such that the secondary fluid flows between the outside nozzle portion and the inner nozzle within the channels. Near the tip of the inner nozzle, the channels can spiral around the outside of the inner nozzle as the channels approach the tip of the inner nozzle. The channels can terminate near the tip of the inner nozzle near where the outer nozzle portion separates from the outside of the inner nozzle to form a small mixing chamber proximate to the tip of the inner nozzle portion where the primary fluid exits the inner nozzle portion. The secondary fluid can interact with the primary fluid exiting the tip of inner nozzle portion such that the primary fluid and secondary fluid leave the housing through a discharge port as a combined fluid flow. The combined fluid flow can be atomized upon exiting the discharge port.

Various alternative embodiments can be utilized to enable the interaction of a primary fluid and a secondary fluid creating a swirl in a mixing chamber so as to produce an atomized spray. A specific embodiment can have secondary fluid channels drilled into an inner nozzle portion from the proximal end of the inner nozzle portion, matching up with holes drilled from the distal end of the inner nozzle, such that the fluid exiting the secondary fluid channels exit the channels with a velocity having a radical component and a component tangent to the outer wall of the inner nozzle portion such that the secondary fluid exits in a spiral fashion. Additional alternative embodiments can deliver the secondary fluid via one or more tubes positioned to project spiraling secondary fluid into the mixing chamber. Other embodiments can incorporate alternative means for delivery of the secondary fluid in accordance with means known to those skilled in the art.

The subject spray nozzle can incorporate a primary fluid manifold which can function as an inlet port for the primary fluid to enter the one or more fluid channels of the inner nozzle. In alternative embodiments, each fluid channel of the inner nozzle portion can be individually served with primary fluid. In a specific embodiment, the subject invention can relate to a vapor atomizer which incorporates a pressure atomizer to initially destabilize a primary fluid wherein the initially destabilized primary fluid then enter a mixing chamber into which a secondary fluid is introduced which further destabilizes the primary fluid such that a combined flow of the primary and secondary fluids is atomized upon exiting the mixing chamber

BRIEF DESCRIPTION OF FIGURES

FIG. 1 shows a heat transfer plate in accordance with the subject invention

FIG. 2 shows an outer nozzle portion housing in accordance with the subject invention.

FIG. 3 shows an inner nozzle portion housing in accordance with the subject invention FIG. 4 shows a primary fluid manifold in accordance with the subject invention.

FIG. 9 shows a heat transfer plate, an outer nozzle portion, an inner nozzle portion, and a primary fluid manifold for a nozzle array assembly in accordance with the subject invention.

FIG. 10 shows another view of the heat transfer plate shown in FIG. 9.

FIGS. 11A-11E show a specific embodiment of a pressure-vapor atomizer in accordance with the subject invention.

DETAILED DESCRIPTION OF THE INVENTION

Figure 5:
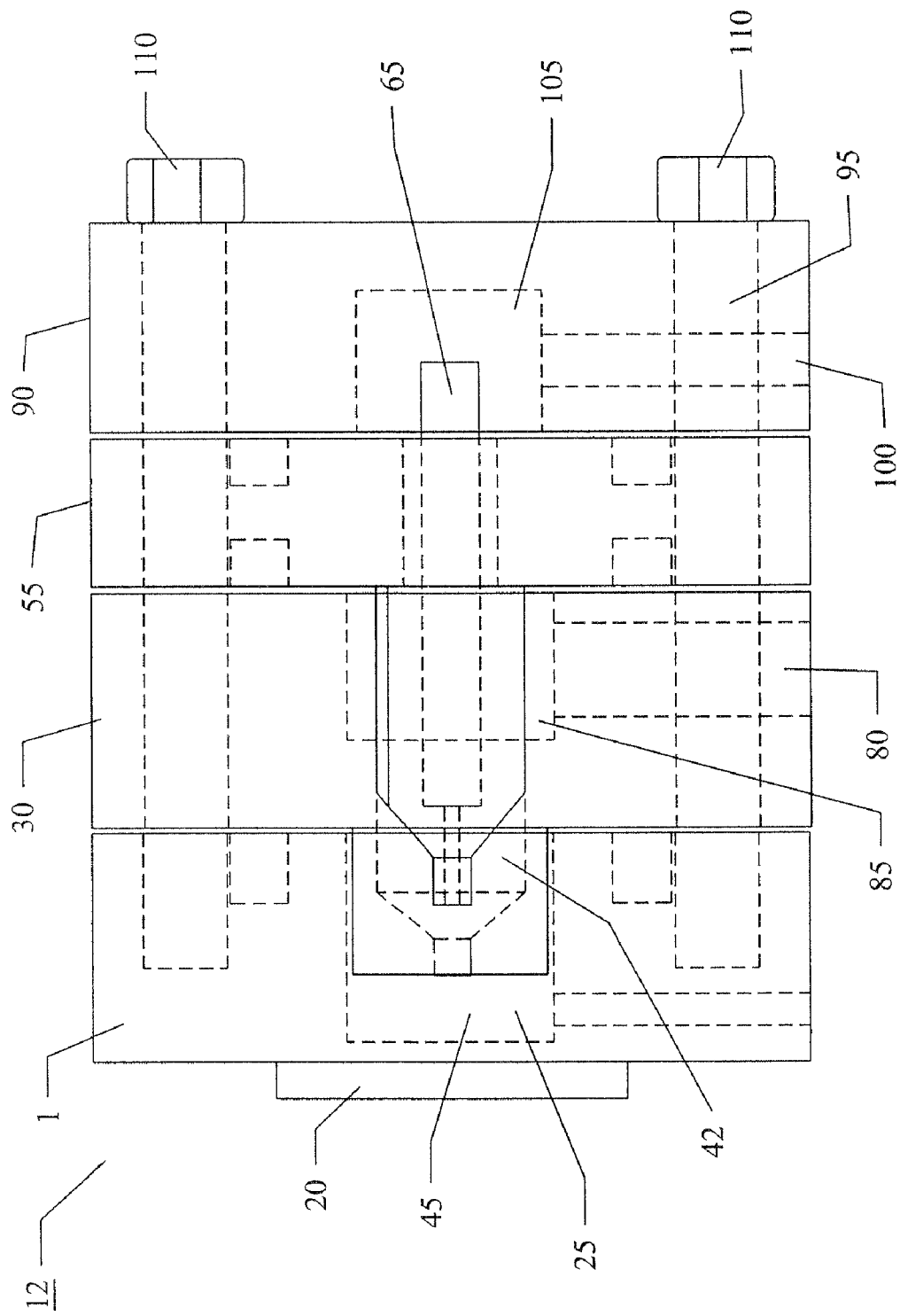
FIG. 5 shows the heat transfer plate of FIG. 1, the outer nozzle portion housing of FIG. 2, the inner nozzle portion housing of FIG. 3, and the primary fluid manifold of FIG. 4 positioned nearly as they would be fastened together in accordance with the subject invention.

The subject invention pertains to a spray nozzle apparatus and method of use. The subject invention also relates to a spray-cooling system and method of use. The subject spray-cooling system can incorporate a spray nozzle and a heat transfer plate. A device to be cooled, such as a laser diode, microwave amplifier, or other high power electrical device, can be placed in direct thermal contact with the heat transfer plate. The transfer of heat between the coolant fluids and the heating device takes place through the heat transfer plate. In a specific embodiment, a cellular heat transfer plate 1, as shown in FIG. 1, can be used. FIGS. 1-4 show various sections of a specific embodiment of the subject invention, with FIG. 5 showing the sections shown in FIGS. 1-4 in a position to be fastened together.

The assembly can be fastened together with a fastening device, such as a bolt, which can be held together with fastener holder 5, such as a threaded bore. Fastener holder 5 can be a simple through hole and another fastener holding mechanism can be used. In an alternative embodiment, the fastening system can be completely external to the assembly in which case fastener holder 5 would not be required. Other methods of fastening may also be utilized, such as brazing, welding, or other means known in the art. To prevent leaking between the parts in the assembly an o-ring 10 or other gasket mechanism can be used.

A heat source 20 can attach to the heat transfer plate 1. The nozzle assembly can then spray coolant fluid into cavity 25. The spray interacts with the rear wall of cavity 25 of the heat transfer plate 1, and heat is transferred from the heat source 20 into the coolant fluid being sprayed.

The spray enters the cavity 25 after exiting the discharge port 40 of the outer nozzle portion 38 as shown in FIG. 2. The outer nozzle portion 38 is held by outer nozzle portion housing 30. A fastening device can hold the nozzle housing 30 in place within the assembly via, for example, apertures 35. The primary coolant flow and the secondary coolant flow coming from the inner nozzle portion 56, held by inner nozzle housing 55, can each enter the inner chamber 42 within the outer nozzle portion housing 30. The two fluid flows can interact and exit the nozzle via discharge port 40. The combined fluids flow out of discharge port 40 and are atomized upon exiting the discharge port 40. The atomized spray is then incident onto heat transfer plate 1. The combined fluids are then heated by the heat transfer plate and, after leaving the surface of the heat transfer plate 1, enter outlet fluid collection chamber 45. The fluid can then exit the assembly via i.e., one or more discharge ports 50.

Figure 7:
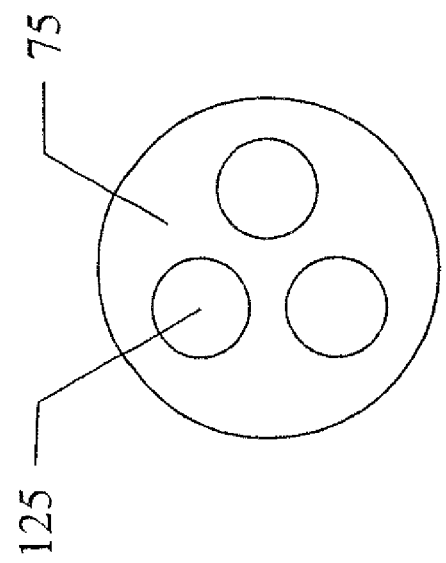
FIG. 7 shows the end of a tip of an inner nozzle portion having three primary fluid channels exiting the tip in accordance with the subject invention.

The inner nozzle portion housing 55, shown in FIG. 3, can also incorporate fastener holes 60 if an internal fastening device is used. Leaks from the assembly port can be controlled with o-rings 10 or other gasket mechanisms. The primary fluid flow can enter one or more fluid channels 65 in the center of the nozzle portion 56 from the primary fluid manifold 90. The primary fluid can flow through the center of the inner nozzle via one or more channels 65. The primary fluid exits the inner nozzle and enters the mixing chamber 42 via inner nozzle tip 75. In specific embodiments, multiple exits ports 125, which are the termination of channels 65, can be utilized with respect to inner nozzle tip 75. In a specific embodiment, the exit ports are positioned such that a symmetric distribution is achieved. Tip 75, as shown in FIG. 7, shows three exit ports 125. In a specific embodiment, each of the three ports can be equidistant from the other two. In a further specific embodiment, the centers of the exit ports 125 can be separated by a distance between about d and about 2 d, where d is the diameter of the exit ports 125. In a specific embodiment, three exit ports are positioned such that the centers of the exit ports are at least 3 d/2 apart, where d is the diameter of the exit ports.

Figure 8:
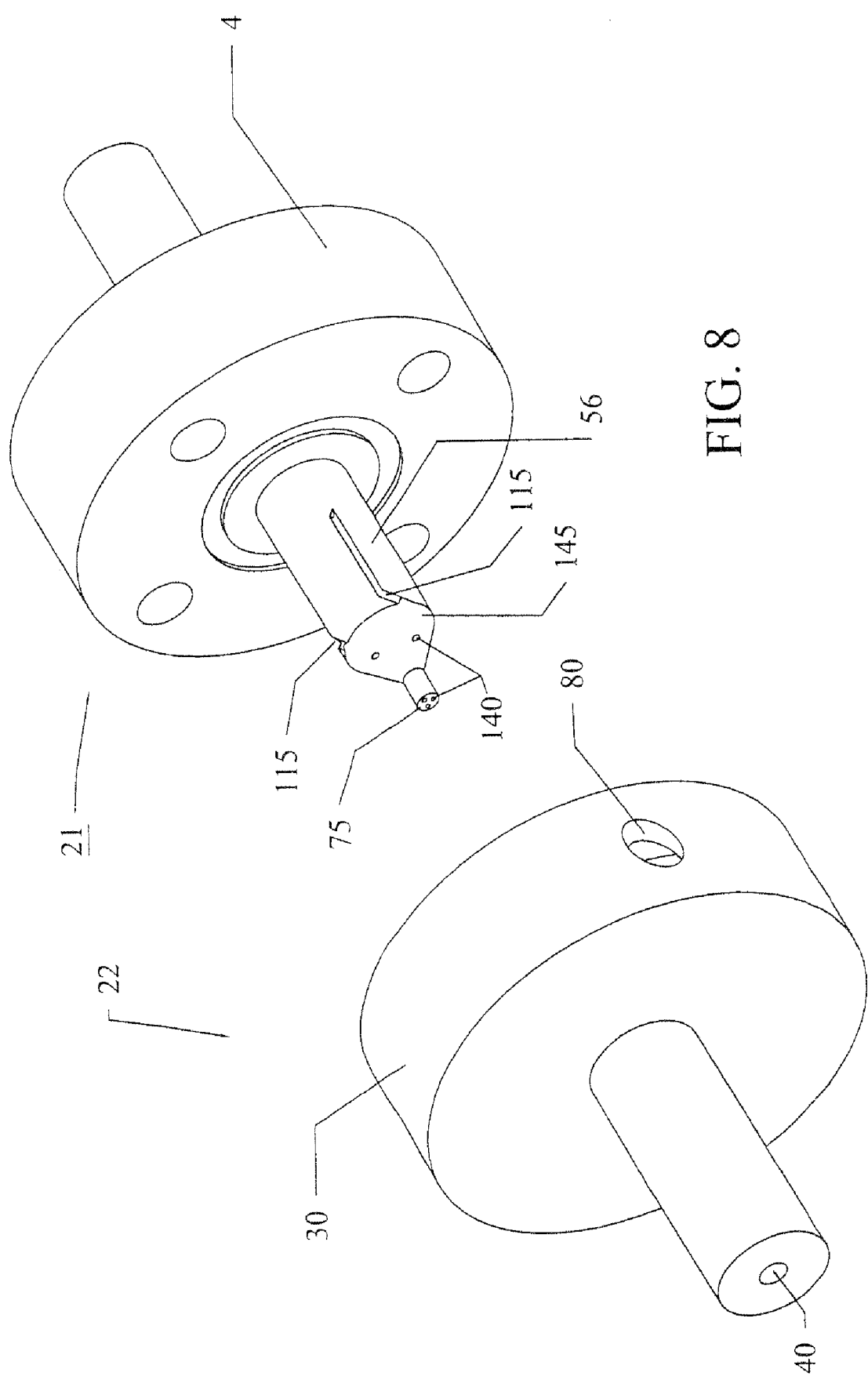
FIG. 8 shows an individual nozzle assembly in accordance with the subject invention.

In alternative embodiments, more or fewer exits ports 125 can be used. Exit ports can also be positioned at other positions, for example near tip 75, in order to introduce initially destabilized primary fluid into mixing chamber 42 such that the secondary fluid introduced into mixing chamber 42 further destabilizes the primary. FIG. 8 shows can embodiment with 3 exit ports 140 on tip 75 and 4 exit ports 140 on the angled wall 145 on the cone shaped portion of inner nozzle portion leading to tip 75. Note, specific embodiments can incorporate primary fluid exit ports 140 at tip and/or other places such as the wall of the cone portion. The primary fluid can be introduced into mixing chamber from these primary fluid exit ports 140 at a variety of angles. In a specific embodiment, primary fluid can exit straight out of tip 75, for example at 0° with respect to the inner nozzle axis. This inner nozzle axis can coincide with an axis of atomization around which a combined flow of primary fluid and secondary fluid is centered upon exiting the discharge port. In additional embodiments, primary fluid can exit at other angles, for example from 0°-90° with respect to the inner nozzle axis. In a specific embodiment, primary fluid exits at an angle between about 0° and about 15° with respect to the inner nozzle axis.

The secondary fluid can enter the secondary fluid cavity 85 via inlet port 80. The secondary fluid then flows into one or more channels 70 cut into the outside of the inner nozzle.

Figure 6:
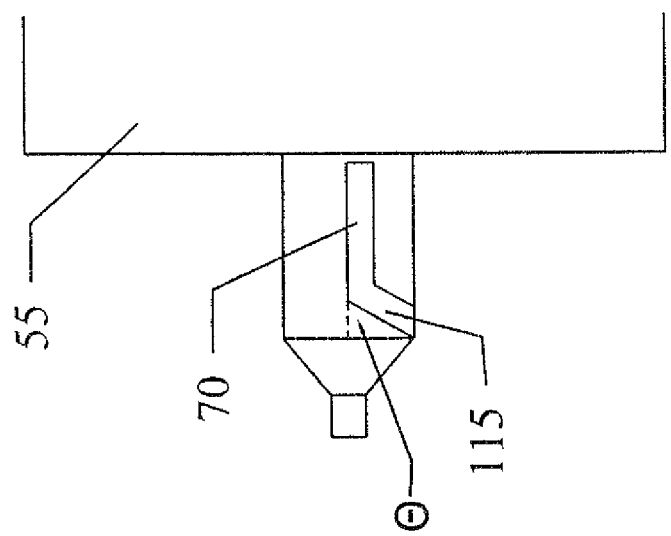
FIG. 6 shows the portion of an inner nozzle portion extending from an inner nozzle housing which shows a secondary fluid channel in accordance with the subject invention.

In a specific embodiment, as the secondary fluid flows in the channels toward the tip of the inner nozzle, the channels can turn from an axial direction, to a more radial direction as shown in FIG. 6. The secondary fluid flowing down channel 70 then changes direction to a more radial flow in the distal portion of the channel 115 and enters the mixing chamber 42. In a specific embodiment, the angle of the channel with respect to the axis of the inner nozzle as the channel terminates into the mixing chamber is selected such that the secondary fluid exiting the channel into the mixing chamber interacts with the primary fluid exiting inner nozzle tip 75 such that the combined fluid flow is atomized upon exiting port 40.

The secondary fluid exiting the end section of channel 115 can further destabilize the primary fluid so as to further increase the surface to volume ratio of the primary fluid. Initial destabilization of the primary fluid can happen when, for example, the primary fluid is separated into a plurality of streams, or otherwise physically destabilized. This initial destabilization allows the secondary fluid to further destabilize the primary fluid with less energy. The physical geometry of the subject mixing chamber allows the further destabilization of the primary fluid with much less energy, supplied by the secondary fluid, than prior techniques. In a specific embodiment, channel 115 makes an angle of between about 0° and about 90° with respect to the axis of atomization as the channel terminates into the mixing chamber 42 such that the secondary fluid exiting the channel enters the mixing chamber at about the same angle. This angle is labeled θ in FIG. 6. In a further specific embodiment, channel 115 can make an angle of between about 45° and about 75° with respect to the axis. In a further specific embodiment, channel 115 can make an angle of about 60° with respect to the axis of the inner nozzle as the channel terminates into the mixing chamber 42.

The primary fluid can enter the inner nozzle portion 56 via a primary fluid manifold 90, shown in FIG. 4. In a specific embodiment fastener holes 95 can be drilled through the primary fluid manifold 90 to allow an internal fastening device to be used to hold the assembly together. The primary fluid can enter the manifold 90 via primary fluid inlet 100. The primary fluid can enter the primary fluid collection chamber 105 before entering the liquid channel 65 of inner nozzle 55.

In a specific embodiment, the assembly, as shown in FIG. 5, can be held together with an internal fastening device 110, such as one or more bolts.

The assembly can incorporate a single nozzle and a single spray chamber 25, or multiple nozzle housings and inner nozzles, for example if the heat transfer plate incorporates multiple spray chambers 25. In alternative embodiments, the secondary fluid manifold can be replaced with a tube connection. In a specific embodiment, the secondary fluid is delivered via a tube for a single nozzle.

Referring to FIG. 2, and to FIG. 9, an important aspect of the nozzle housing is the discharge orifice 40 diameter and the diameter of the outer tip of the outer nozzle portion 38 which surrounds the discharge orifice. The outer tip diameter controls how close individual nozzles can be positioned, and needs to be at least as big as the diameter of mixing chamber 42. In a specific embodiment, the outer tip diameter is 7 mm, so as to allow multiple nozzles in an array to spray into individual 10 $mm^2$ cells when the remaining features on the nozzles are appropriately sized. In this embodiment, the discharge orifice 40 diameter is 1.25 mm and the insert cavity of outer nozzle portion 38 which receives the inner nozzle portion (shown in FIG. 3) is 5 mm, while the part of inner nozzle portion 56 inserted into the outer nozzle portion 38 has an outer diameter of 4.95 mm. The part of inner nozzle portion inserted into the outer nozzle portion is inserted such that the tip 75 of the insert is 1.25 mm from the flush end of the discharge orifice so as to create the mixing chamber 42 shown in FIG. 5. In a specific embodiment of a nozzle array, for example as shown in FIG. 9, the nozzles can be positioned such that the spacing of adjacent nozzles discharge orifices 40 is between about 3 mm and about 30 mm. In a further specific embodiment, such spacing can be between about 5 mm and about 15 mm. In a further specific embodiment, the spacing can be about 10 mm.

Referring to FIG. 8, an embodiment of the subject invention incorporating a single nozzle is shown. FIG. 8 shows two sections of the nozzle which are equivalent in functionality to the sections shown in FIGS. 2 and 3. A first piece 21 of the nozzle comprises an inner nozzle portion 56 having a center channel 65 running from a proximal end of inner nozzle portion to a distal end of the inner nozzle portion, such that the center channel terminates at tip 75 of inner nozzle portion 56. FIG. 8 also shows alternative locations for the termination of the central channel on the angled wall 145 on the cone-shaped portion of the inner nozzle portion leading to 75. Although FIG. 8 shows entry ports for primary fluid into the mixing chamber on tip 75 and the angled wall 145 on the cone shaped portion of the inner nozzle portion, such ports can be location only on the tip, only on the cone-shaped portion, both, or other location which allows the primary to enter the mixing chamber so as to properly interact with the secondary fluid entering the mixing chamber. A second piece 22 of the nozzle comprises an outer nozzle portion 38 having a discharge port 40 and housing a mixing chamber 42. As the inner nozzle portion 56 is inserted into outer nozzle portion 38, the inner nozzle portion 56 fits snuggly into an inside cylindrical wall of the outer nozzle portion 56 which extend from the distal end of channels 70 to a location which does not reach the proximal end of channels 70. Accordingly, secondary fluid entering secondary fluid inlet port 80 travels through the housing 30 of the outer nozzle portion into secondary fluid cavity 85 which allows the secondary fluid to contact the inner nozzle portion 56 from the inner nozzle housing 55 to past the proximal end of channels 70. As the inside wall of the outer nozzle portion 56 is snuggly in contact with the inner nozzle portion 56 over a portion of channels 70, the secondary fluid enters channels 70 where the inside wall of the outer nozzle portion stops contacting the inner nozzle portion 56 and travels within channels 70 toward the distal end of the inner nozzle portion 56.

As the secondary fluid nears the distal end of inner nozzle portion, the outer wall of the inner nozzle portion tapers in toward tip 75 creating mixing chamber 42 between the inside wall of outer nozzle portion 38 and the tapered or cone-shaped portion and tip of inner nozzle portion 56. In the embodiments shown in FIG. 8 and FIGS. 2 and 3, the inside wall of outer nozzle portion 38 tapers from a point near the axial position of tip 75 toward discharge port 40, with the taper angle being about the same as the taper angle of the distal end of inner nozzle portion 56. Mixing chamber 42 can extend past the termination of tip 75. As the secondary fluid nears the taper portion of inner nozzle portion 56, channels 70 are positioned to spiral around the outer wall of inner nozzle portion such that the secondary fluid leaving the distal end of channels 70 enters mixing chamber 42 with a velocity which includes a component in the axial direction and a component which is tangential to the cylindrical outer wall of the inner nozzle portion. As the secondary fluid enters the mixing chamber 42 it collides with the inside wall of outer nozzle portion 38, which is the wall of mixing chamber 42, and creates a swirl effect so as to further destabilize the primary fluid exiting tip 75 of inner nozzle portion 56. The destabilized combined fluid flow of the primary fluid and secondary fluid are then atomized upon exiting discharge port 40 of mixing chamber 42.

Although a variety of droplet sizes and velocities can be produced in accordance with the subject invention, in a specific embodiment an atomizing spray nozzle can produce droplets having mean diameters in a range from about 10 microns to about 200 microns and provides the droplets a velocity in a range from about 5 meters per second to about 50 meters per second. Preferably, the size and velocity of the particles are such that the effects of gravity are negligible. Producing small droplets at high velocity can allow the method and apparatus of the subject invention to be used with heated surfaces 2 oriented in a variety of directions (e.g. vertical or horizontal) and can make it easier to provide coverage of the surface 2 with the spray coolant.

Referring to FIGS. 9 and 10, and embodiment of the subject invention incorporating a plurality, or array, of nozzles is shown. Each of the individual nozzles can operate in much the same way as an individual nozzle in accordance with the subject invention, for example as shown in FIGS. 2, 3, and 8. The embodiment shown in FIGS. 9 and 10 can also be used for a single nozzle, and the embodiment shown in FIGS. 1-5 can incorporate a plurality of nozzles. In comparing this embodiment with the embodiment shown in FIGS. 1-5, secondary fluid enters the inner nozzle portion 56 housing in FIG. 9, while the secondary fluid enters the outer nozzle portion housing 38 in FIG. 5, and the heated fluid exits through the outer nozzle portion housing in FIG. 9 while the heated fluid exits through the heat transfer plate in FIG. 5. Other embodiments can port these fluids in different ways as well. Primary and secondary fluids can be delivered to this array of nozzles via one or more entry ports on the housing of the nozzle array assembly such that the plurality of nozzles can be spaced closer together than individual nozzle assemblies, as shown for example in FIGS. 1-5 and FIG. 8, could be placed.

Although the nozzle array assembly shown in FIG. 9 is serviced with fluids from the side of the assembly, in alternative embodiment, the assembly can be serviced from the proximal end of the assembly. Servicing the assembly from the proximal end can allow a plurality of nozzle array assemblies to be positioned adjacent to each other, again potentially more closely positioned than a plurality of nozzle array assemblies which can be serviced from the side. In a specific embodiment, the subject nozzle array can allow adjacent nozzles to be positioned sufficiently close together such that the distance between discharge ports 40 of adjacent nozzles is between about 3 mm and about 30 mm. In a further specific embodiment, such spacing is between about 5 mm and about 15 mm. In a further specific embodiment, such spacing is about 10 mm.

Referring to FIG. 9, four sections are shown. A first section, primary fluid manifold 90, houses primary fluid collection chamber 105 and primary fluid inlet 100. Primary fluid enters primary fluid collection chamber 105 through primary inlet 100 and enters primary fluid channel 65 at the proximal end of inner nozzle portion 56. Primary fluid travels through inner nozzle portion 56 and exits the distal end of inner nozzle portion 56 at tip 75. Secondary fluid enters one or more secondary fluid inlet ports 86 and enters one or more channels 70 on each of the plurality of inner nozzle portions 56 in the same way as described with the embodiment in FIGS. 1-5 and FIG. 8. The plurality of inner nozzle portions are held in portion by inner nozzle portion housing 55. Inner nozzle portion housing 55 also incorporates a wall to prevent secondary fluid from entering primary fluid chamber 105. As described with respect to FIG. 8, secondary fluid travels in one or more channels 70 in the outer wall of each of the inner nozzle portions 56 into mixing chamber 42 so as to interact with primary fluid exiting tip 75. The further destabilized combined fluid flow exits discharge port 40 of outer nozzle portion 38. This combined fluid flow can be atomized upon exiting discharge port 40. The atomization can begin with initially destabilized primary fluid entering the mixing chamber from the inner nozzle portion, can continue with the interaction of the primary and secondary fluids in the mixing chamber, and can further continue as the combined fluid flow exits discharge port 40, such that the combined fluid flow is atomized upon exiting discharge port 40.

This atomized fluid then enters a corresponding compartment 16 of cellular heat transfer plate 15. The atomized fluid then interacts with the walls of compartment 16 and heat is transferred to the atomized fluid. In this way, heat from heat source 20 can be transferred through a wall of heat transfer plate 15 to the atomized fluid. The heated fluid is then discharged via one or more discharge ports 50. In alternative embodiments, the heated fluid can flow to the atmosphere such that discharge ports 50 are not needed. In addition, the atomized spray can be sprayed onto other types of surfaces from which heat is to be removed or can just be sprayed into the air.

With respect to the subject invention, for example in the embodiment shown in FIGS. 1-5, 8, 9, and 11, the primary fluid can be a liquid, such as water or other liquid coolant, and the secondary fluid can be a gas, such as air or other gaseous coolant. In alternative embodiments, the primary fluid can be a gas, liquid, or mixture thereof and the secondary fluid can also be a gas, liquid, or mixture thereof.

In a specific embodiment of the subject invention, a pressure-vapor atomizer can incorporate two separate nozzles, or nozzle stages where a first nozzle, such as a pressure atomizer, can initial destabilize a primary fluid. The output from this first nozzle stage can then be inputted to the second nozzle stage for further destabilization. Referring to FIGS. 11A-11D, an example of such a pressure-vapor atomizer is shown. A first nozzle, or nozzle stage, can be a pressure atomizer 220. The pressure atomizer 220 can have an entry port 201. The primary fluid can flow through entry port 201 out of port 220 where the primary fluid can be distributed around the outside area between the tip of the pressure atomizer 220 and the pressure atomizer housing, 230. A portion of the primary fluid can then flow into radial channels, 3. Another portion of the primary fluid can flow through axial direction port 205. The portion of the primary fluid from radial channels 203 and the portion of the primary fluid from port 205 can combine and exit the pressure atomizer 220 via exit port 207 as a destabilized, or pre-atomized, fluid. The combined initially destabilized primary fluid exiting port 207 can be inputted to second nozzle stage, such as a vapor atomizer 240. The pressure atomized primary fluid can flow from exit port 207 into swirl, or mixing, chamber 209. A secondary fluid, such as vapor, can enter the vapor atomizer via port 208 and distribute in, preferably, equal portions to radial flow direction channels 211. The vapor exiting the radial flow direction channels 211 can collect in the swirl chamber 209 so as to create a swirl effect, wherein the swirling vapor combines with the destabilized primary fluid entering the swirl chamber from exit port 207. A portion of the primary fluid entering the swirl chamber from exit port 207 can be atomized. The secondary fluid entering chamber 209 than further destabilizes the primary fluid entering chamber 209. The combined flows in the swirl chamber can exit the pressure-vapor atomizer via exit port 12.

In a specific embodiment, the subject nozzle sprays evenly onto an essentially circular area having a diameter of about 10 mm at a distance of about 13 mm from the tip of the nozzle. Table I provides comparison data for two of the best commercially available vapor atomizers two nozzles and a specific embodiment (RTI) of the subject invention. The subject nozzle (RTI) provides a much higher quality spray at much lower energy costs. The energy required for producing a spray comes from the pressures and flow rate of the vapor and liquid entering the nozzle. Therefore, the lower the pressure and flow rate the more efficient the nozzle operates, providing that the performance of the atomization is similar.

TABLE I

|  | SU12 | SU22B | RTI |
|---|---|---|---|
| Hole size (mm) | 0.762 | 1.067 | 0.356 |
| Overall size H × D (mm) | 25.4 × 22.8 | 25.4 × 22.8 | 13.1 × 6.2 |
| Pressure Drop (psi) | 10 | 10 | 10 |
| Vapor Flow rate at 10 psi (scfh) | 29 | 87 | 4 |
| Mass flux (g/sec) | 1.05 | 1.05 | 1.05 |

Figure 12A:
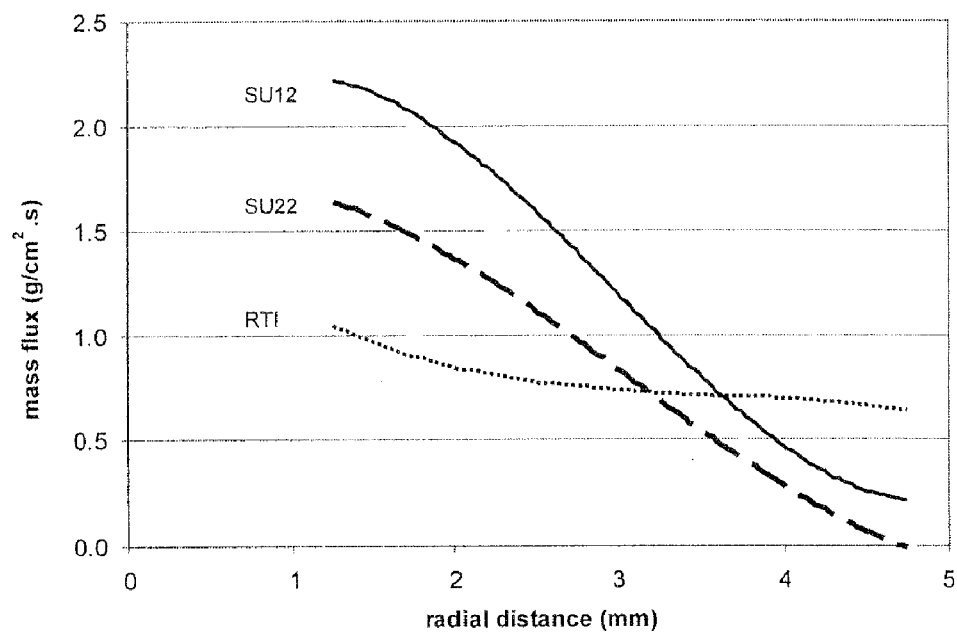
FIG. 12A shows a plot of mass flux versus radical distance for a specific embodiment of the subject invention and two prior art spray nozzles.

Nozzle performance can be quantified by the distribution of the sprayed liquid on a particular target. The three nozzles characterized in Table I were tested for spray distribution. Ideally, the distribution of the sprayed liquid would be perfectly even over the target area. FIG. 12A shows a plot of the mass flux distribution versus radial distance (10 psi, 1 gph water) for the three nozzles in Table I. The two commercially available nozzles are the SU12 and SU22 nozzles from Spray Systems, Inc. The SU12 produces an uneven distribution, with the highest mass flux (~1.6 g/cm$^2$ sec) occurring in the center of spray pattern. The spray pattern has decreasing mass flux moving away from the center of the spray pattern toward the edge of the spray pattern. The mass flux reaches approximately zero at a radial distance of about 4.75 mm from the center of the spray pattern at a distance of about 10 mm from the tip of the nozzle.

Figure 12B:
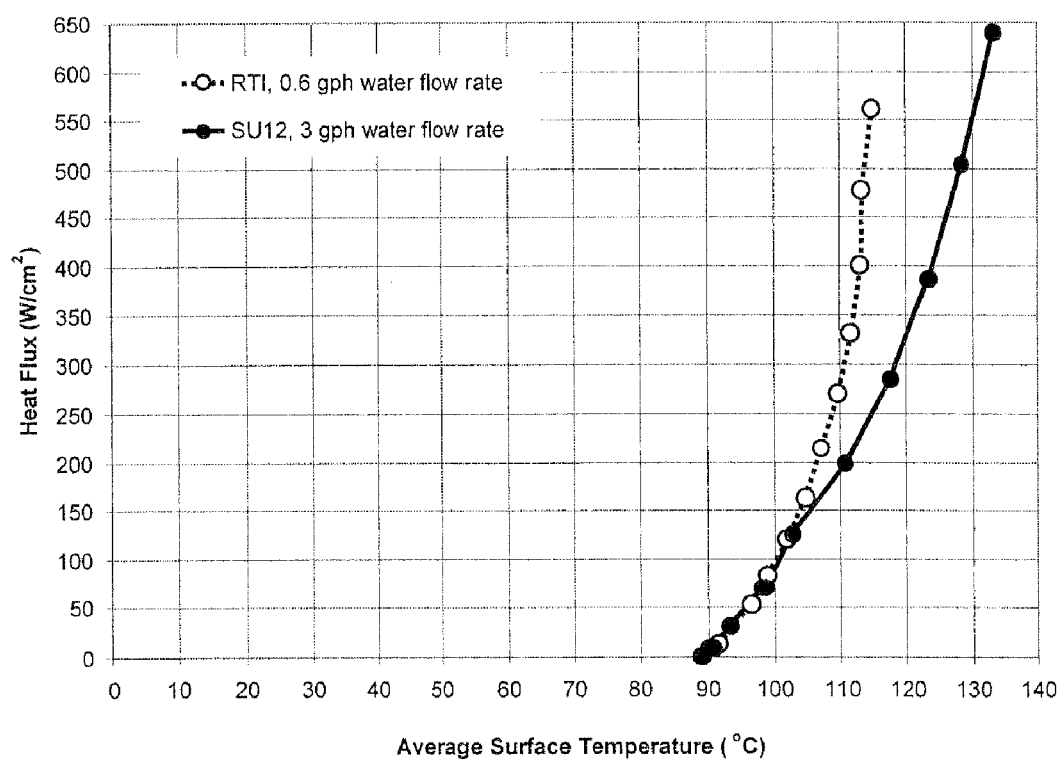
FIG. 12B shows a plot of heat flux versus average surface temperature for a specific embodiment of the subject invention and a prior art spray nozzle

The SU22B nozzle produces an uneven distribution, with the highest mass flux rate (~2.2 g/cm$^2$ sec) in the center of the spray pattern. The spray pattern has decreasing mass flux moving away from the center of the spray toward the edge of the spray pattern and approaching essentially zero at the edge of the spray pattern. In contrast, the specific embodiment of the subject nozzle (RTI) referenced in Table I produces a more even spray pattern. Although, the mass flux is higher in the center of the spray pattern, which is cone-shaped, the variation of mass flux is less than about 40% across the spray pattern. The results of spray cooling with the specific embodiment and a prior art nozzle are shown in FIG. 12B. FIG. 12B shows a plot of heat flux versus average surface temperature for the subject nozzle (RTI) in Table I and the SU12 nozzle.

EXAMPLE

Surface Area Enhancement for Heat Transfer Surfaces

Figure 13:
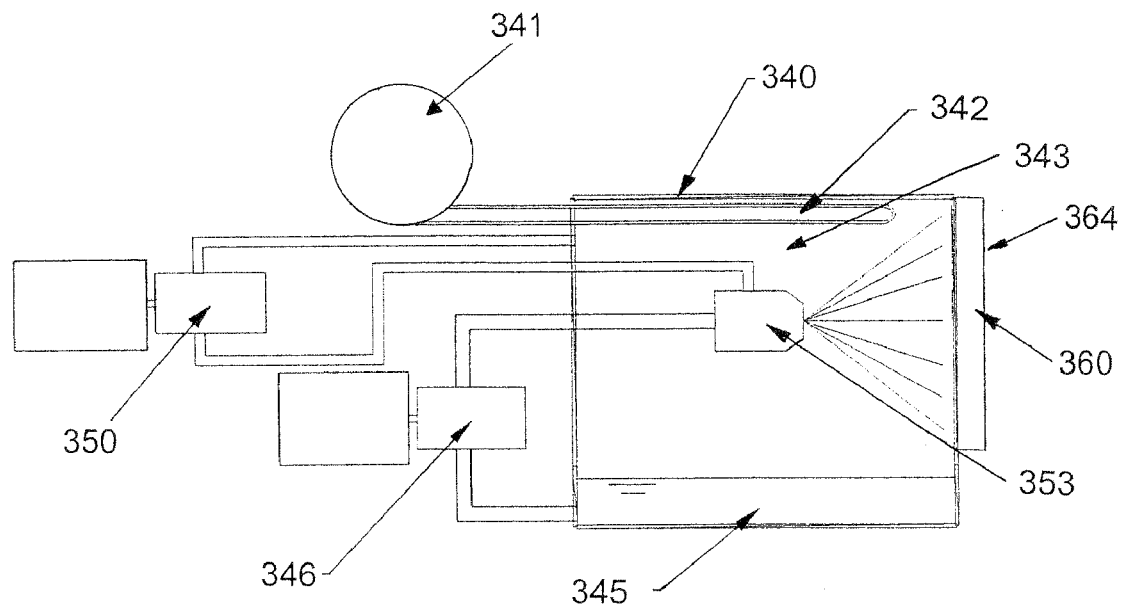
FIG. 13 shows a schematic diagram of a cooling system in accordance with the subject invention.

The subject invention also relates to a heat transfer apparatus having an enhanced surface which can increase the rate of heat transfer from the surface to an impinging fluid. The subject enhanced surface can be incorporated with any of the heat transferred surfaces disclosed in the subject patent application or incorporated with other heat transfer surfaces. The subject invention also pertain to heat transfer apparatus, such as heat transfer plates, which incorporate the subject enhanced surfaces. The subject enhanced surfaces can also be utilized for heat desorbtion from a surface. In a specific embodiment, the subject system can comprise: a housing, a fluid pump or compressor, a nozzle array consisting of one or more nozzles, and a high heat flux source interface plate. The process begins with the housing. The housing contains the working fluid. The process as shown in FIG. 13 begins with the entire assembly placed within a housing 340. The housing is then filled with the desired coolant to a level which allows an adequate pumping reservoir 345 without impending on the coolant flow. A pump or compressor draws the coolant from the housing and pressurizes it. The pressurized coolant is forced through the nozzle array. The nozzles atomize the coolant onto the heated surface. The surface is enhanced to increase the effective cooling area of the spray.

Evaporative spray cooling is enhanced by maintaining the thinnest liquid layer possible on the heat transfer surface. Pressure atomizer nozzles use high pressure liquid and vapor atomizer nozzles use compressed vapor to atomize the liquid coolant. Both types of nozzles can be used to produce a high velocity and lower droplet density spray. The result is a spray of liquid coolant onto the extended surface area which takes advantage of the additional surface area.

The pump 346 draws in the liquid coolant and pressurizes it to the desired pressure. The pressurized liquid goes to the liquid inlet port of spray nozzle 353. Compressor 350 draws in coolant vapor and pressurizes it to the desired pressure. The pressurized coolant vapor is sent to the vapor inlet port on spray nozzle 353. The compressed vapor and the pressurized liquid coolant combine in nozzle 353 to form small liquid droplets with a high velocity.

The spray nozzle 353 can be a vapor atomizer nozzle as shown using both compressed vapor and liquid coolant or a pressure atomizer nozzle, not shown, which uses only pressurized liquid.

Figure 14A:
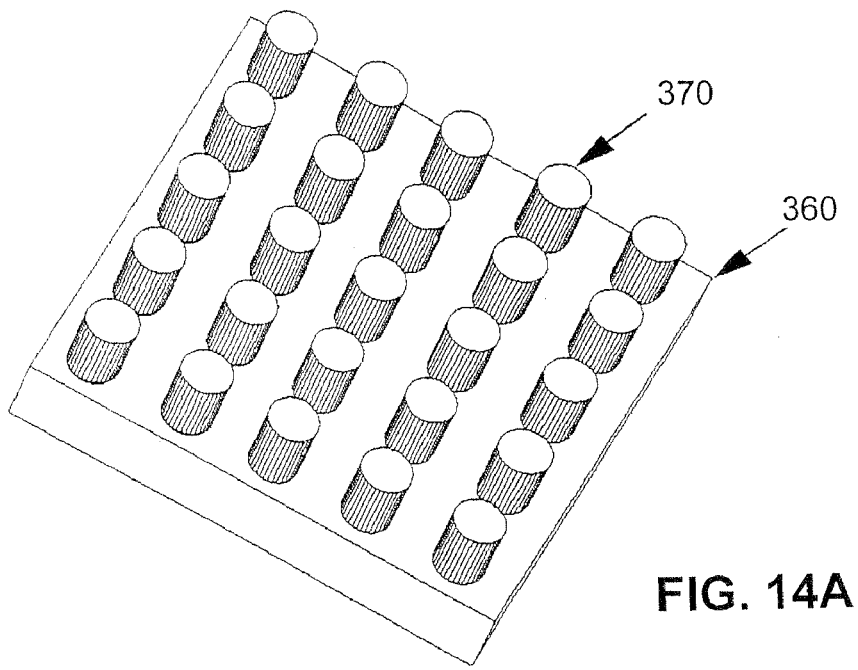
FIGS. 14A-14E show a heat transfer surface incorporating surface enhancement in accordance with the subject invention.
Figure 14B:
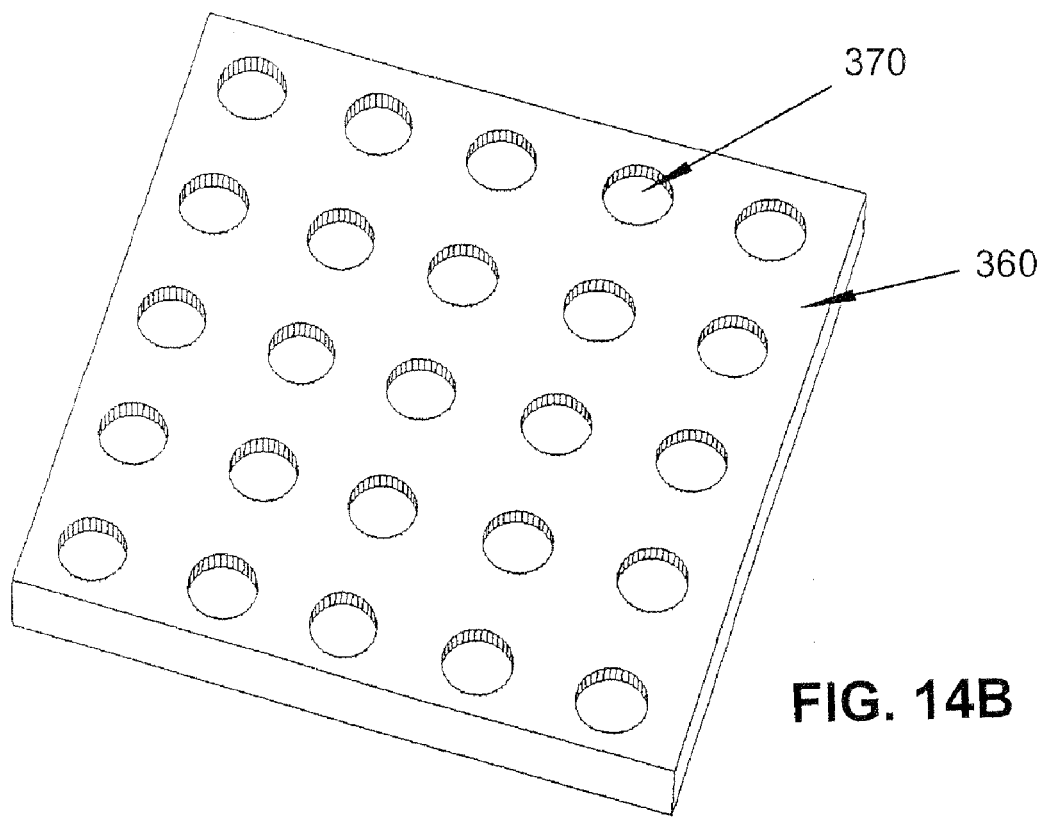
Figure 14C:
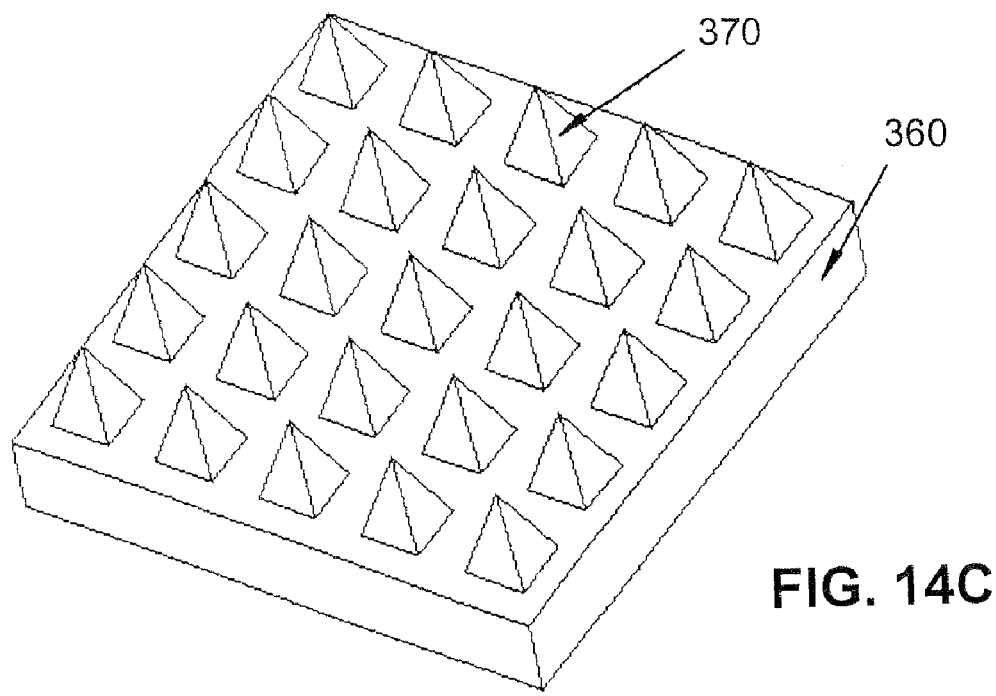
Figure 14D:
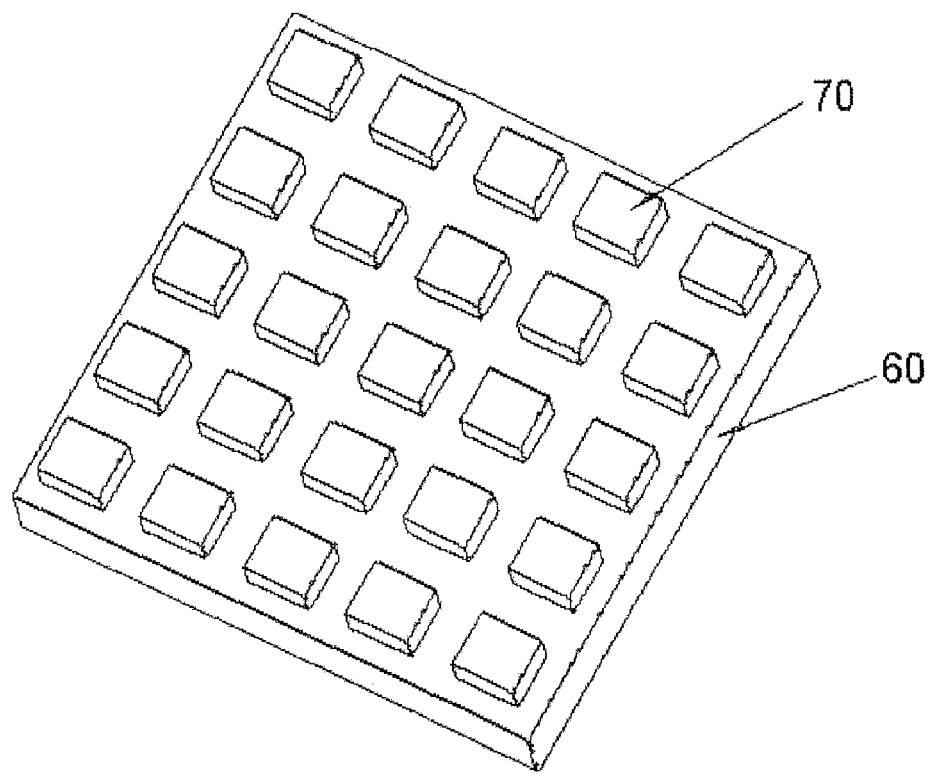
Figure 14E:
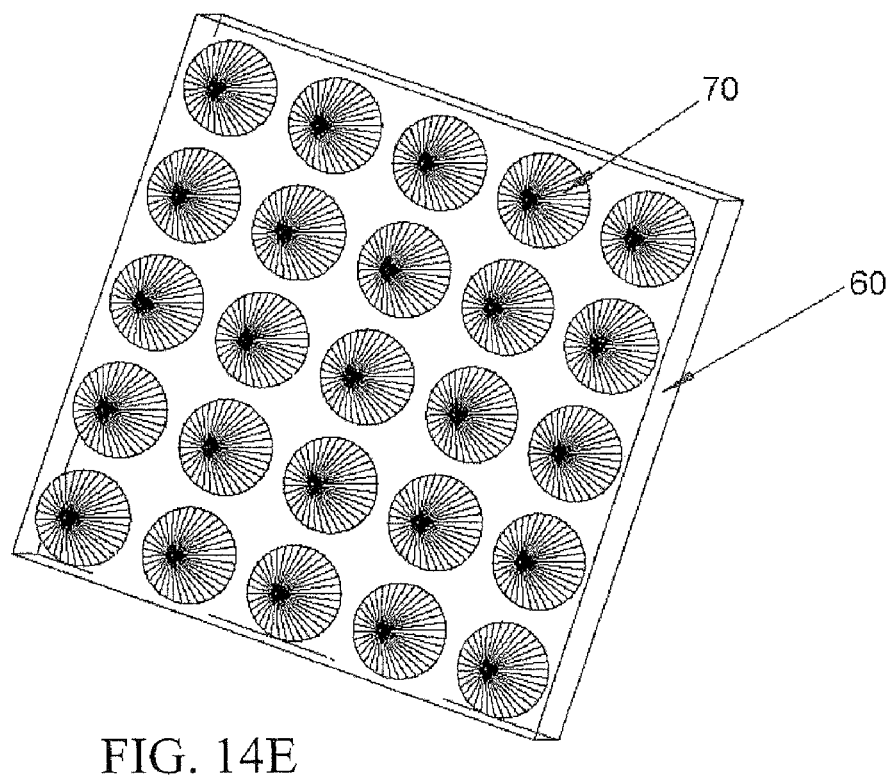

The droplets impinge on cooling plate 360. Multiple surface area enhancements 370 are connected to cooling plate 360 as shown in FIGS. 14A-14E. The enhancements can be milled into or extend from the surface or can be thermally attached to the surface 360. The enhancements can be protrusions from surface 360 as shown in FIG. 14A or indentations into surface 360 as shown in FIG. 14B. The enhancements can be of any shape including but not limited to rods, cubes, cones, or pyramids. FIGS. 14A-14E show variations of possible surface enhancements that improve spray cooling. However, any geometric shape or combination of shapes intruded into and extended from the surface can be used as surface enhancements. The surfaces can also be sandblasted to increase the heat transfer properties of the surface.

In a specific embodiment, protrusions, and/or indentations, having a height and/or depth, to diameter ratio of between about 0 to about 10 can be utilized. In further specific embodiments, a height, and/or depth, to diameter ratio of between about 1 and about 5 can be utilized. In another embodiment, protrusions, and/or indentations, having a height to spacing between adjacent protrusions, and/or indentations, ratio of between about 2 and 4 can be utilized. In a further embodiment, a height, and/or depth, to diameter ratio of about 3 can be utilized. In a specific embodiment, the number of protrusions, and/or indentations, density/spray cooling area is between about 1 and about 100 per square centimeter. In a further specific embodiment, the number of protrusions, and/or indentations, density/spray cooling area is between about 10 and about 20 per square centimeter. In a specific embodiment, the subject surface enhancements can increase the surface area, as compared to a smooth surface, by about 1 to about 5 times. In a further specific embodiment, the subject surface enhancements can increase the surface area by about 1.1 to about 2. In a specific embodiment, the center to center spacing of the subject protrusions, and/or indentations is between about (0.1) d and about 10 d, where d is the diameter (or mean diameter) of the protrusions, and/or indentations. In a further specific embodiment, the center to center spacing is about d. In a specific embodiment, the roughness of the subject enhanced surface can have a RMS of between about optically smooth and about 100 micrometers.

The vapor coolant can then flow to a condenser, such as coil 342. The vapor condenses on the condenser coil 342 and forms liquid. The liquid then flows into reservoir 345. A heat extractors 341, removes the heat from the condenser 342 via thermal connection 340. The heat extraction can be a refrigeration cycle or an ambient heat exchanger.

A series of control devices including thermocouples, flow meters and level indicators are used to control the process in order to maintain the desired operating conditions.

Sample and embodiments described herein are for illustrative purposes only and various modifications or changes in light thereof will be suggested to persons skilled in the art and are to be included within the spirit and purview of this application and the scope of the appended claims.

The invention claimed is:

1. A method of removing heat from a heated surface, comprising:
   providing a mixing chamber;
   guiding a primary fluid to the mixing chamber;
   guiding a secondary fluid to the mixing chamber, wherein the secondary fluid enters the mixing chamber with a direction of travel which causes the secondary fluid to interact with the primary fluid, wherein the interaction of the secondary fluid with the primary fluid causes destabilization of the primacy and/or the secondary fluid;
   discharging a combined flow of the primary fluid and the secondary fluid through a discharge port of the mixing chamber, wherein the combined flow of the primary fluid and the secondary fluid is atomized upon exiting the discharge port; and
   spraying the combined flow of the primary fluid and the secondary fluid exiting the mixing chamber through the discharge port onto a heated surface, wherein the combined flow sprayed onto the heated surface absorbs heat from the heated surface and carries the absorbed heat away as the combined flow leaves the heated surface,
   wherein guiding a primary fluid to the mixing chamber comprises guiding the primary fluid to the mixing chamber via at least one primary fluid channel, wherein guiding a secondary fluid to the mixing chamber comprises guiding the secondary fluid to the mixing chamber via at least one secondary fluid channel, further comprising:
   providing an inner nozzle portion, wherein the at least one primary fluid channel allows primary fluid to flow through the inner nozzle portion; and
   providing an outer nozzle portion,
   wherein an outer surface of the inner nozzle portion has at least one groove cut into the outer surface, wherein the inner nozzle portion is inserted into a cavity of the outer nozzle portion such that an inner surface of the outer nozzle covers a portion of each groove cut into the outer surface of the inner nozzle portion to form one of the at least one secondary fluid channel, wherein a portion of the cavity of the outer nozzle portion remaining after insertion of the inner nozzle portion into the outer nozzle portion, surrounded by the inner surface of the outer nozzle portion and the outer surface of the inner nozzle portion, forms the mixing chamber.

2. The method according to claim 1,
   wherein the combined flow of the primary fluid and the secondary fluid has an axis of atomization around which the combined flow is centered upon exiting the discharge port, wherein the secondary fluid enters the mixing chamber at an angle to the axis of atomization so as to generate a swirl effect in the mixing chamber.

3. The method according to claim 1, wherein the primary fluid comprises a liquid.

4. The method according to claim 1, wherein the primary fluid is a liquid.

5. The method according to claim 4, wherein the secondary fluid is a gas.

6. The method according to claim 1, wherein the primary fluid is a mixture of a gas and a liquid.

7. The method according to claim 1, wherein the secondary fluid is a mixture of a gas and a liquid.

8. The method according to claim 1, wherein guiding a primary fluid to the mixing chamber causes a plurality of streams of primary fluid to enter the mixing chamber.

9. The method according to claim 8, wherein the plurality of streams of primary fluid are axially symmetric.

10. The method according to claim 8, wherein the combined flow of the primary fluid and the secondary fluid has an axis of atomization around which the combined flow is centered upon exiting the discharge port, wherein the plurality of streams of primary fluid are not parallel with the axis of atomization.

11. The method according to claim 8, wherein the combined flow of the primacy fluid and the secondary fluid has an axis of atomization around which the combined flow is centered upon exiting the discharge port, wherein the plurality of streams enter the mixing chamber at an angle of between about 0° and about 15° with respect to the axis of atomization.

12. The method according to claim 1, wherein the primary fluid enters the mixing chamber with a direction of travel substantially toward the discharge port.

13. The method according to claim 1, wherein the secondary fluid comprises a gas.

14. The method according to claim 1, wherein the secondary fluid comprises a liquid.

15. The method according to claim 8, wherein the plurality of streams are sufficiently spaced apart such that each of the plurality of streams acts as an independent stream.

16. The method according to claim 9, wherein each of the plurality of streams of primary fluid are each approximately equidistance from each of the other streams.

17. The method according to claim 16, wherein guiding a primary fluid to the mixing chamber causes three streams of primary fluid to enter the mixing chamber.

18. The method according to claim 16, wherein the distance from the center of each of the plurality of streams to the center of each adjacent stream is between about d and about 2 d, where d is the diameter of each stream.

19. The method according to claim 16, wherein the distance from the center of each of the plurality of streams to the center of each adjacent stream is at least about 3 d/2 where d is the diameter of each stream.

20. The method according to claim 1, wherein the secondary fluid enters the mixing chamber at an angle between about 0° and about 90° with respect to the axis of atomization.

21. The method according to claim 1, wherein the secondary fluid enters the mixing chamber of an angle between about 45° and about 75° with respect to the axis of atomization.

22. The method according to claim 8, wherein the plurality of streams of primary fluid enters the mixing chamber at an angle between about 0° and about 15° with respect to the axis of atomization.

23. The method according to claim 1, wherein the velocity of the combined flow of the primary fluid and the secondary fluid which is atomized upon exiting the discharge port is between approximately 5 meters per second and approximately 50 meters per second.

24. The method according to claim 1, wherein the combined flow of the primary fluid and the secondary fluid which is atomized upon exiting the discharge port comprises droplets having mean diameters in a range from about 10 microns to about 200 microns.

25. The method according to claim 1, wherein the heated surface comprises surface enhancements which increases the heat transfer between the combined flow sprayed onto the heated surface and the heated surface.

26. The method according to claim 25, wherein the heated surface comprises surface enhancements which increase the surface area of the heated surface by a factor between about 1 and about 5.

27. The method according to claim 26, wherein the surface enhancements increase the surface area of the heated surface by a factor between about 1.1 and about 2.

28. The method according to claim 1, wherein guiding the primary fluid to the mixing chamber comprises inputting primary fluid into a primary fluid inlet port, wherein guiding the secondary fluid to the mixing chamber comprises inputting the secondary fluid into a secondary fluid inlet port, wherein the combined flow leaves the heated surface and is outputted from the spray nozzle via a heated fluid discharge port.

29. The method according to claim 1, wherein spraying the combined flow of the primary fluid and the secondary fluid exiting the mixing chamber through the discharge port onto the heated surface comprises spraying the combined flow of the primary fluid and the secondary fluid exiting the mixing chamber through the discharge port onto a first surface of an interface plate, wherein the interface plate comprises a second surface in thermal contact with a heat source.

30. The method according to claim 1, further comprising:
providing at least one additional mixing chamber;
guiding the primary fluid to each of the at least one additional mixing chamber;
guiding the secondary fluid to each of the at least one additional mixing chamber, wherein the secondary fluid enters each of the at least one additional mixing chamber with a direction of travel which causes the secondary fluid to interact with the primary fluid, wherein the interaction of the secondary fluid with the primary fluid causes atomization of the primary and/or the secondary fluids; and
discharging a combined flow of the primary fluid and the secondary fluid via a corresponding at least one additional discharge port, wherein the combined flow of the primary fluid and the secondary fluid is atomized upon exiting each of the corresponding at least one additional discharge port.

31. The method according to claim 30, wherein guiding the primary fluid to each of the at least one additional mixing chamber causes a corresponding at least one additional plurality of streams of primary fluid to enter each of the corresponding at least one additional mixing chamber.

32. A method of removing heat from a heated surface, comprising:
providing a mixing chamber;
guiding a primary fluid to the mixing chamber;
guiding a secondary fluid to the mixing chamber, wherein the secondary fluid enters the mixing chamber with a direction of travel which causes the secondary fluid to interact with the primary fluid, wherein the interaction of the secondary fluid with the primary fluid causes destabilization of the primary and/or the secondary fluid,
discharging combined flow of the primary fluid and the secondary fluid through a discharge port of the mixing chamber, wherein the combined flow of the primary fluid and the secondary fluid is atomized upon exiting the discharge port; and
spraying the combined flow of the primary fluid and the secondary fluid exiting mixing chamber through the discharge port onto a heated surface, wherein the combined flow sprayed onto the heated surface absorbs heat from the heated surface and carries the absorbed heat away as the combined flow leaves the heated surface, further comprising:
destabilizing the primary fluid prior to guiding the primary fluid to the mixing chamber.

33. The method according to claim 32,
wherein destabilizing the primary fluid prior to guiding the primary fluid to the mixing chamber is accomplished via a pressure atomizer.

34. The method according to claim 32, wherein destabilizing the primary fluid prior to guiding the primary fluid to the mixing chamber comprises:
providing a second mixing chamber;
guiding a first portion of the primary fluid to the second mixing chamber; guiding a second portion of the primary fluid to the second mixing chamber;
wherein interaction of the first portion of the primary fluid and the second portion of the primary fluid in the mixing chamber destabilizes the first portion of the primary fluid and/or the second portion of the primary fluid; and
discharging a combined flow of the first portion of the primary fluid the second portion of the primary fluid through a second discharge port of the second mixing chamber, wherein the combined flow of the first portion of the primary fluid and the second portion of the primary fluid is destabilized upon exiting the second discharge port, wherein the combined flow exiting the second discharge port is inputted to the mixing chamber.

35. The method according to claim 34,
wherein guiding the first portion of the primary fluid to the second mixing chamber comprises guiding the first portion of the primary fluid to the second mixing chamber via a channel, wherein guiding a second portion of the primary fluid to the second mixing chamber comprises guiding the second portion of the primary fluid to the second mixing chamber via a plurality of channels that cause the second portion of the primary fluid to enter the second mixing chamber so as to generate a swirl effect in the second mixing chamber.

36. The method according to claim 32,
wherein the combined flow of the primary fluid and the secondary fluid has an axis of atomization around which the combined flow is centered upon exiting the discharge port, wherein the secondary fluid enters the mixing chamber at an angle to the axis of atomization so as to generate a swirl effect in the mixing chamber.

37. The method according to claim 32, wherein the primary fluid comprises a liquid.

38. The method according to claim 32, wherein the primary fluid is a liquid.

39. The method according to claim 38, wherein the secondary fluid is a gas.

40. The method according to claim 32, wherein the primary fluid is a mixture of a gas and a liquid.

41. The method according to claim 32, wherein the secondary fluid is a mixture of a gas and a liquid.

42. The method according to claim 32, wherein guiding a primary fluid to the mixing chamber causes a plurality of streams of primary fluid to enter the mixing chamber.

43. The method according to claim 42, wherein the plurality of streams of primary fluid are axially symmetric.

44. The method according to claim 42, wherein the combined flow of the primary fluid and the secondary fluid has an axis of atomization around which the combined flow is centered upon exiting the discharge port, wherein the plurality of streams of primary fluid are not parallel with the axis of atomization.

45. The method according to claim 42, wherein the combined flow of the primary fluid and the secondary fluid has an axis of atomization around which the combined flow is centered upon exiting the discharge port, wherein the plurality of streams enter the mixing chamber at an angle of between about 0° and about 15° with respect to the axis of atomization.

46. The method according to claim 32, wherein the primary fluid enters the mixing chamber with a direction of travel substantially toward the discharge port.

47. The method according to claim 32, wherein the secondary fluid comprises a gas.

48. The method according to claim 32, wherein the secondary fluid comprises a liquid.

49. The method according to claim 42, wherein the plurality of streams are sufficiently spaced apart such that each of the plurality of streams acts as an independent stream.

50. The method according to claim 43, wherein each of the plurality of streams of primary fluid are each approximately equidistance from each of the other streams.

51. The method according to claim 50, wherein guiding a primary fluid to the mixing chamber causes three streams of primary fluid to enter the mixing chamber.

52. The method according to claim 50, wherein the distance from the center of each of the plurality of streams to the center of each adjacent stream is between about d and about 2 d, where d is the diameter of each stream.

53. The method according to claim 50, wherein the distance from the center of each of the plurality of streams to the center of each adjacent stream is at least about 3 d/2 where d is the diameter of each stream.

54. The method according to claim 32, wherein the secondary fluid enters the mixing chamber at an angle between about 0° and about 90° with respect to the axis of atomization.

55. The method according to claim 32, wherein the secondary fluid enters the mixing chamber at an angle between about 45° and about 75° with respect to the axis of atomization.

56. The method according to claim 42, wherein the plurality of streams of primary fluid enters the mixing chamber at an angle between about 0° and about 15° with respect to the axis of atomization.

57. The method according to claim 32, wherein the velocity of the combined flow of the primary fluid and the secondary fluid which is atomized upon exiting the discharge port is between approximately 5 meters per second and approximately 50 meters per second.

58. The method according to claim 32, wherein the combined flow of the primary fluid and the secondary fluid which is atomized upon exiting the discharge port comprises droplets having mean diameters in a range from about 10 microns to about 200 microns.

59. The method according to claim 32, wherein guiding a primary fluid to the mixing chamber comprises guiding the primary fluid to the mixing chamber via at least one primary fluid channel.

60. The method according to claim 59, wherein guiding a secondary fluid to the mixing chamber comprises guiding the secondary fluid to the mixing chamber via at least one secondary fluid channel.

61. The method according to claim 32, wherein the heated surface comprises surface enhancements which increases the heat transfer between the combined flow sprayed onto the heated surface and the heated surface.

62. The method according to claim 61, wherein the heated surface comprises surface enhancements which increase the surface area of the heated surface by a factor between about 1 and about 5.

63. The method according to claim 62, wherein the surface enhancements increase the surface area of the heated surface by a factor between about 1.1 and about 2.

64. The method according to claim 32, wherein guiding the primary fluid to the mixing chamber comprises inputting primary fluid into a primary fluid inlet port, wherein guiding the secondary fluid to the mixing chamber comprises inputting the secondary fluid into a secondary fluid inlet port, wherein the combined flow leaves the heated surface and is outputted from the spray nozzle via a heated fluid discharge port.

65. The method according to claim 32, wherein spraying the combined flow of the primary fluid and the secondary fluid exiting the mixing chamber through the discharge port onto the heated surface comprises spraying the combined flow of the primary fluid and the secondary fluid exiting the mixing chamber through the discharge port onto a first surface of an interface plate, wherein the interface plate comprises a second surface in thermal contact with a heat source.

66. The method according to claim 32, further comprising:
providing at least one additional mixing chamber;
guiding the primary fluid to each of the at least one additional mixing chamber;
guiding the secondary fluid to each of the at least one additional mixing chamber, wherein the secondary fluid enters each of the at least one additional mixing chamber with a direction of travel which causes the secondary fluid to interact with the primary fluid, wherein the interaction of the secondary fluid with the primary fluid causes atomization of the primary and/or the secondary fluids; and
discharging a combined flow of the primary fluid and the secondary fluid via a corresponding at least one additional discharge port, wherein the combined flow of the primary fluid and the secondary fluid is atomized upon exiting each of the corresponding at least one additional discharge port.

67. The method according to claim 66, wherein guiding the primary fluid to each of the at least one additional mixing chamber causes a corresponding at least one additional plurality of streams of primary fluid to enter each of the corresponding at least one additional mixing chamber.

* * * * *

UNITED STATES PATENT AND TRADEMARK OFFICE
CERTIFICATE OF CORRECTION

| | | |
|---|---|---|
| PATENT NO. | : 8,104,533 B2 | Page 1 of 1 |
| APPLICATION NO. | : 12/237003 | |
| DATED | : January 31, 2012 | |
| INVENTOR(S) | : Daniel P. Rini, Guochang Zhao and R. Randolph Anderson | |

It is certified that error appears in the above-identified patent and that said Letters Patent is hereby corrected as shown below:

Column 8,
Lines 23-24, "held in portion" should read --held in position--.

Column 10,
Line 24, "also pertain" should read --also pertains--.
Line 27, "heat desorbtion" should read --heat desorption--.

Column 12,
Line 56, "primacy fluid" should read --primary fluid--.

Column 13,
Line 16, "about 3 d/2" should read --about 3d/2--.
Line 22, "of an angle" should read --at an angle--.

Column 16,
Line 11, "about 3 d/2" should read --about 3d/2--.

Signed and Sealed this
First Day of May, 2012

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 8,104,533 B2 |
| APPLICATION NO. | : 12/237003 |
| DATED | : January 31, 2012 |
| INVENTOR(S) | : Daniel P. Rini, Guochang Zhao and H. Randolph Anderson |

Page 1 of 1

It is certified that error appears in the above-identified patent and that said Letters Patent is hereby corrected as shown below:

Column 8,
Lines 23-24, "held in portion" should read --held in position--.

Column 10,
Line 24, "also pertain" should read --also pertains--.
Line 27, "heat desorbtion" should read --heat desorption--.

Column 12,
Line 56, "primacy fluid" should read --primary fluid--.

Column 13,
Line 16, "about 3 d/2" should read --about 3d/2--.
Line 22, "of an angle" should read --at an angle--.

Column 16,
Line 11, "about 3 d/2" should read --about 3d/2--.

This certificate supersedes the Certificate of Correction issued May 1, 2012.

Signed and Sealed this
Nineteenth Day of June, 2012

David J. Kappos
*Director of the United States Patent and Trademark Office*